United States Patent [19]

Stier et al.

[11] Patent Number: 4,601,898

[45] Date of Patent: Jul. 22, 1986

[54] AQUEOUS SOLUTION CONTAINING TIF$_4$ AND CHELATING AGENT

[75] Inventors: Roger E. Stier, Clifton, N.J.; William H. Dunn, Brooklyn, N.Y.; James D. Vidra, Lebanon, N.J.

[73] Assignee: Beecham Inc., Clifton, N.J.

[21] Appl. No.: 716,491

[22] Filed: Mar. 27, 1985

[51] Int. Cl.$^4$ ..................... A61K 7/18; A61K 33/16
[52] U.S. Cl. ..................................... 424/52; 424/151
[58] Field of Search ................................. 424/52, 151

[56] References Cited

U.S. PATENT DOCUMENTS

| | | | |
|---|---|---|---|
| 3,751,568 | 8/1973 | Mundorff et al. | 424/52 |
| 3,885,028 | 5/1975 | Cella et al. | 424/52 |
| 4,157,387 | 6/1979 | Benedict | 424/52 |
| 4,291,017 | 9/1981 | Beierle et al. | 424/52 |
| 4,418,053 | 11/1983 | Muhler et al. | 424/52 |

Primary Examiner—Shep K. Rose
Attorney, Agent, or Firm—Jacobs & Jacobs

[57] ABSTRACT

An anti-caries aqueous solution, which comprises an aqueous solution containing an anti-caries effective amount of TiF$_4$ and a chelating agent in an amount effective to stablilize the TiF$_4$, said solution having a pH of at least about 3.5.

14 Claims, No Drawings

AQUEOUS SOLUTION CONTAINING TIF₄ AND CHELATING AGENT

The present invention relates to an aqueous solution containing an anti-caries effective amount of $TiF_4$.

Titanium tetrafluoride has been reported as providing greater reduction of enamel solubility and greater protection against animal caries than comparable levels of other fluorides, as well as forming a glaze on the teeth. Shresta et al., Enamel Dissolution: I. Effects of Various Agents and Titanium Tetrafluoride, J. Dent. Res. 51,1561–1566, 1972 and II. Action of Titanium Tetrafluoride, J. Dent. Res. 51, 1567–1571, 1972. In the patent literature, $TiF_4$ is used in the form of a 1% aqueous solution having a pH of about 1.5, see, e.g. Mundorf et al., U.S. Pat. No. 3,751,568, but this highly acidic solution may result in marked irritation to the mouth unless carefully applied, and hence the use of $TiF_4$ has been suggested for annual or semi-annual applications of a 1% aqueous solution of $TiF_4$ by a dentist. Prior efforts to provide $TiF_4$ in other than the highly acidic 1% solution have not been successful, because $TiF_4$ is unstable in aqueous media at a pH above 3.0 and this coupled with its potential for irritation has prevented the use of $TiF_4$ in consumer products.

The present invention now provides an aqueous solution comprising an anti-caries effective amount of $TiF_4$ and an amount of a chelating agent effective to stabilize the $TiF_4$. Since the $TiF_4$ is stabilized by the chelating agent, the solution of the present invention has the required stability to be sold to the consumer using conventional over-the-counter channels of trade.

Furthermore, the aqueous solution of the present invention avoids the low pH at which conventional aqueous $TiF_4$ solutions are employed, and hence the skin irritation arising from the prior art $TiF_4$ solutions is also avoided. This is an important factor in a consumer product, since repeated use and lack of care would make skin irritations more pronounced. The consumer can now use the $TiF_4$-containing aqueous solution of the invention on a daily basis instead of being limited to annual treatments with $TiF_4$ by a dentist.

In addition to the advantage of enhanced fluoride uptake, the solution of the invention also forms a protective glaze on the teeth in the form of an organo-metallic complex. when the amount of $TiF_4$ is at least about 1.0% by weight, based on the total composition. This glaze renders the teeth more acid-resistant and may desensitize exposed dentin by sealing exposed dentin tubules. This latter effect may protect susceptible teeth against root caries.

The aqueous solution of the invention comprises a chelating agent to stabilize $TiF_4$ in the aqueous solution and thereby prevent decomposition of the $TiF_4$. A wide range of chelating agents may be used in the present invention, particularly those containing chelating hydroxy, carboxy and/or sulfonic acid groups, ethylenediaminetetraacetic acid, salicyclic acid, citric acid, 2,4 and 2,6-dihydroxybenzoic acids, dihydroxytartaric acid, nitrilotriacetic acid, tartaric acid, 4,5-dihydroxy-1,3-benzenedisulfonic acid, mandelic acid, malic acid, mellitic acids, oxalic acid and acetic acid. The acid groups may be in the form of the free acid or metal salt thereof. Alternatively, the chelating agent may be added in the form of a metal chelate, particularly a di- or trivalent metal chelate. Examples of such metal chelates include complexes of $\beta$-diketones with aluminum and chromium, for example aluminium and chromium triacetylacetonates, and ethylene diamine tetraacetic acid complexes of zinc and copper. It is presently preferred to use tartaric acid or citric acid or their alkali metal salts, or other chelating agents containing both chelating hydroxy and carboxy groups.

The amount of the chelating agent will generally be from about 0.10 to about 15%, preferably from about 0.30 to about 6.0%, of the solution. It is presently preferred that the ratio of the chelating agent to the $TiF_4$ be from about 1:1 to about 5:1 or more, preferably from about 2:1 to about 4:1.

The aqueous solution of the present invention also comprises an anti-caries effective amount of $TiF_4$. Preferably, the solution will provide at least 250 ppm F to obtain an anti-caries effect and hence the amount of $TiF_4$ in the solution will preferably be at least about 0.04%, such as from about 0.04 to about 2.5%, and most preferably from about 0.12 to about 1.0%.

One preferred embodiment of the invention provides from about 0.10 to about 0.30% of $TiF_4$ and from about 0.10 to about 1.5% of said chelating agent, by weight based on the total composition.

Another preferred embodiment of the invention provides from about 1.0 to about 2.5% $TiF_4$ and from about 1.0 to about 12.5% of said chelating agent, by weight based on the total composition.

The aqueous solution of the present invention may be used as an anti-caries dentifrice or mouthrinse, and may contain alcohol, humectants, such as glycerin, aqueous sorbitol, polyethylene glycol or polypropylene glycol and surfactants, including cationic, anionic and nonionic surfactants. When present, it is suitable to use from about 6 to about 25% alcohol, from about 3 to about 15% humectant and from about 0.5 to about 2.5% surfactant.

Other materials may be added, such as soluble saccharin, flavoring oils (e.g. oils of spearmint, wintergreen, peppermint), coloring agents, menthol, chlorophyll compounds (e.g. sodium copper chlorophyllin), and anti-bacgerial agents (e.g. chlorhexidine). These materials, when present, will be in minor amounts, such as up to about 4%, e.g. from about 0.05 to about 3% in total.

The aqueous solution of the invention is prepared in the usual manner by dissolving the ingredients in water to form a solution. The pH of the solution will generally be from between about 3.5 and about 5.5. The aqueous solution whether formulated as a dentifrice or mouthrinse, is used in a conventional manner by placing a small portion in the mouth and swirling the solution into contact with the teeth and gums, after which the solution is expelled.

In a preferred embodiment of the invention, the $TiF_4$ is admixed with an aqueous solution of the chelating agent to solubilize the $TiF_4$, and then the remaining ingredients are combined with the mixture of $TiF_4$ and the chelating agent.

The present invention is illustrated in terms of its preferred embodiments in the Examples that follow. In this specification and claims, all parts and percentages are by weight, unless otherwise stated.

EXAMPLE 1

|  | PERCENT |
|---|---|
| Titanium Tetrafluoride | 0.163 |

| | PERCENT |
|---|---|
| Sodium Citrate | 0.50 |
| Surfactant (Pluronic F-127) | 1.50 |
| Flavor | 0.25 |
| Dye (0.1% aq. solution) | 1.00 |
| Sodium Saccharin | 0.10 |
| Deionized Water | q.s |

The chelating agent was dissolved in water and the $TiF_4$ was added and solubilized, after which sodium saccharin, flavor and dye were added. An aqueous solution of pH of 5.0 was obtained for use as an anti-caries dentifrice.

EXAMPLE 2

| | PERCENT |
|---|---|
| Alcohol | 10.0 |
| Titanium Tetrafluoride | 0.163 |
| Surfactant (Pluronic F-127) | 1.75 |
| Sodium Citrate | 0.5 |
| Humectant (glycerin) | 5.3 |
| Sweetener | 0.05 |
| Preservative | 0.025 |
| Dye | 0.0045 |
| Flavor | 0.21 |
| Deionized Water | q.s |

Following the procedure of Example 1, the above ingredients were combined to form a solution for use as an anti-caries mouthrinse. The aqueous solution had a pH of 5.0.

The $TiF_4$-containing composition of the present invention also has the unexpected advantage of providing greater uptake of fluoride in teeth than products using sodium fluoride or sodium monofluorophosphate. In addition, the composition of the present invention also provides increased titanium uptake as well.

We claim:

1. An anti-caries aqueous solution, consisting essentially of an aqueous solution containing an anti-caries effective amount in the range of from about 0.04 to about 2.5% of $TiF_4$ and a chelating agent in an amount of from about 0.10 to about 15% and effective to stabilize the $TiF_4$, said solution having a pH of from about 3.5 to about 5.5, the percentages being by weight based on the total weight of the solution.

2. The aqueous solution according to claim 1, wherein the weight ratio of said chelating agent to said $TiF_4$ is from about 1:1 to about 5:1.

3. The aqueous solution according to claim 1, wherein said chelating agent is selected from the group consisting of chelating agents having one or more chelating hydroxy, carboxy or sulfonic acid groups and metal chelates.

4. The aqueous solution according to claim 1, which comprises from about 0.10 to about 0.30% of $TiF_4$ and from about 0.10 to about 1.5% of said chelating agent, by weight based on the total composition.

5. The aqueous solution according to claim 1, which comprises from about 1.0 to about 2.5% $TiF_4$ and from about 1.0 to about 12.5% of said chelating agent, by weight based on the total composition.

6. The aqueous solution according to claim 1, wherein said chelating agent is selected from the group consisting of ethylenediaminetetraacetic acid, salicyclic acid, citric acid, 2,4 and 2,6-dihydroxybenzoic acids, dihydroxytartaric acid, nitrilotriacetic acid, tartaric acid, 4,5-dihydroxy-1,3-benzenedisulfonic acid, mandelic acid, malic acid, mellitic acids, oxalic acid, acetic acid and metal chelates or a mixture of two or more thereof.

7. The aqueous solution according to claim 1, wherein said chelating agent contains chelating hydroxy and carboxy groups.

8. The aqueous solution according to claim 7, wherein the chelating agent is tartaric acid, citric acid or an alkali metal salt thereof.

9. The aqueous solution according to claim 4, wherein said chelating agent contains chelating hydroxy and carboxy groups.

10. The aqueous solution according to claim 1, in the form of an anti-caries mouthrinse and further comprising alcohol, a humectant and a surfactant.

11. The aqueous solution according to claim 9, wherein the chelating agent is tartaric acid, citric acid or an alkali metal salt thereof.

12. The aqueous solution according to claim 5, wherein said chelating agent contains chelating hydroxy and carboxy groups.

13. The aqueous solution according to claim 4, wherein said chelating agent is tartaric acid, citric acid or an alkali metal salt thereof.

14. The aqueous solution according to claim 5, wherein said chelating agent is tartaric acid, citric acid or an alkali metal salt thereof.

* * * * *